(12) United States Patent
Megerle

(10) Patent No.: US 6,834,533 B2
(45) Date of Patent: Dec. 28, 2004

(54) SYSTEM AND METHOD FOR DETECTING BIO-HAZARDOUS PARTICULATES IN MAIL HANDLING SYSTEMS

(75) Inventor: Clifford A. Megerle, Thousand Oaks, CA (US)

(73) Assignee: Lockheed Martin Corporation, Bethesda, MA (US)

(*) Notice: Subject to any disclaimer, the term of this patent is extended or adjusted under 35 U.S.C. 154(b) by 0 days.

(21) Appl. No.: 10/279,312

(22) Filed: Oct. 24, 2002

(65) Prior Publication Data

US 2004/0020264 A1 Feb. 5, 2004

Related U.S. Application Data

(60) Provisional application No. 60/330,807, filed on Oct. 31, 2001.

(51) Int. Cl.[7] .................................................. G01M 3/04
(52) U.S. Cl. ..................... 73/45.4; 73/23.41; 73/864.33
(58) Field of Search ........................... 73/864.33, 23.41, 73/863.71, 863.22, 45.4, 19.01, 864.71, 864.91; 229/71; 232/17, 30, 31; 250/455.11; 340/540; 358/1.15, 402; 422/22, 24, 292; 705/1, 406; 713/201

(56) References Cited

U.S. PATENT DOCUMENTS 5,786,530 A * 7/1998 Fenlon ........................ 73/49.3
6,105,419 A * 8/2000 Michels et al. ............... 73/49.3
2002/0124664 A1 * 9/2002 Call et al. ................. 73/863.22
2003/0085348 A1 5/2003 Megerle ...................... 250/287
2003/0152480 A1 8/2003 Sham .......................... 422/28
2003/0167740 A1 9/2003 Murphy ....................... 55/337
2004/0022670 A1 * 2/2004 Megerle et al. ............... 422/28

OTHER PUBLICATIONS

WO 03/085373, Published PCT International Application, Publication Date Oct. 16, 2003, PCT/US02/35984 (12078–154PCT).
International Search Report, Nov. 20, 2003, PCT/US02/34514 (12078–198PCT).
WO 03/078957, Published PCT International Application, Publication Date Sep. 25, 2003, PCT/US02/34514 (12078–198PCT).

* cited by examiner

Primary Examiner—Hezron Williams
Assistant Examiner—John Fitzgerald
(74) Attorney, Agent, or Firm—Perkins Smith & Cohen LLP; Jacob N. Erlich, Esq.; Harvey Kaye

(57) ABSTRACT

A system and method for detecting bio-hazardous particulates in mail handling systems includes an air intake hood 20 that connects to a biohazard sensing suite 24 which, in turn, connects through an outlet duct 26 to a filter, adsorber, or scrubber 28 that removes any bio-hazardous material prior to exhausting the air. An air mover 30 is located in the outlet duct 26 and moves the air into the air intake hood 20 into the biohazard sensing suite 24. The biohazard sensing suite 24 detects the presence of any undesired bio-hazardous material.

14 Claims, 5 Drawing Sheets

SYSTEM AND METHOD FOR DETECTING BIO-HAZARDOUS PARTICULATES IN MAIL HANDLING SYSTEMS

CROSS-REFERENCE TO RELATED APPLICATIONS

The present application claims the priority of previously filed provisional application Ser. No. 60/330,807 filed Oct. 31, 2001 for System and Method For Detecting Biohazard Particulates In Mail Handling Systems, the content of which is incorporated herein by reference.

FIELD OF THE INVENTION

The present invention relates generally to a system and method for detecting biohazard materials in mail handling systems and, more particularly, to a system and method that detects biohazard materials, especially particulates, in mail handling systems at that point or points in the handling process having the greatest probability of expelling or expressing the biohazard material into the ambient air.

BACKGROUND OF THE INVENTION

Mail of the type characterized "letter" mail, i.e., mail that is contained within envelopes of various sizes is processed by mail handling and sorting machines that transport the individual "pieces" using various types of conveyers, drive rollers, pinch rollers, belts, and the like to move the pieces along various tracks, chutes, and paths while address information is being scanned to allow sorting and routing of the piece.

Some mail pieces have been known to contain dangerous biohazard materials, including particulates, such as anthrax spores. In addition to seeking to expose the addressee to the biohazard material, the biohazard-containing piece also contaminates other mail pieces being handled in the mail transport system and also contaminates the machinery, vehicles, and physical plants that are used to process the mail.

U.S. Published application Ser. No. US 2002/0126008 published Sep. 12, 2002 and filed Oct. 31, 2001 discloses use of sensors at various locations within a typical mail processing system to sense the presence of a harmful agent. This system is completely open to the ambient atmosphere. (The present application is based upon a provisional patent application filed Oct. 31, 2001.)

U.S. Published application Ser. No. US 2002/0124664 published Sep. 12, 2002 and filed Feb. 1, 2002 discloses use of a mail sampling system used in a room separate from the remainder of a post office facility and in which there is an air intake fan and all outgoing air is filtered before release. Most often openings are formed in the parcels and mail for the sampling. The sampling system is said to determine whether mail is contaminated with a chemical or biological agent. (The present application is based upon a provisional patent application filed Oct. 31, 2001.)

U.S. Pat. Nos. 5,942,699 and 6,324,927 disclose a manner of collective sampling of cargo items for contaminants such as chemical residues. The cargo items are placed into a special airtight chamber and physically agitated, such as by vibration, to release particulates and vapors from the items, and bursts of high pressure air is sent into the chamber. Heated air may also be used.

U.S. Pat. No. 3,915,339 discloses use of pressurized air into a container to loosen and cause free flow of material therein move.

U.S. Pat. No. 3,998,101 discloses a method and apparatus for sampling the atmosphere in non-hermetically-sealed containers by enclosing baggage in a chamber and varying the air pressure cyclically to mix a portion of the air in the baggage with the air in the chamber and a vapor detector is used to detect the presence of explosives or drugs in the baggage.

U.S. Pat. No. 4,580,440 discloses a method of detecting a contraband substance in freight cargo in which the container is agitated to disturb particulates therein and samples are taken of the air containing such particulates. The collected particulates are heated to drive off vapors indicative of the contraband substance and the vapors are analyzed in a mass analyzer.

U.S. Pat. No. 4,718,268 discloses a method and apparatus for detecting a contraband substance in freight cargo similar to that of U.S. Pat. No. 4,580,440 mentioned above.

U.S. Pat. No. 4,764,351 discloses a sterilization method and apparatus using a gaseous agent for sterilizing a gas for use in treating materials.

U.S. Pat. No. 5,322,603 discloses a method of an apparatus for treating infections medical wastes is which large sizes of medical waste in a sealed body are exposed to microwaves and heat.

U.S. Pat. No. 5,470,546 discloses apparatus for storing and sterilizing bio-hazardous waste in which air is evacuated and pressurized steam is injected.

U.S. Pat. No. 5,591,117 discloses a method and an apparatus for the disposal of material containing infective microorganisms such as bacteria, fungi and viruses by introducing the material into a container which can be charged with ozone and exposed to the action thereof until the microorganisms are killed, and then the ozone is discharged from the container and converted to a lower valence level and the container is then evacuated.

U.S. Pat. No. 5,700,426 discloses a method for decontaminating or sterilizing "in situ" a vacuum sealed container and device for implementing such method for sterilizing or decontaminating microorganisms or dangerous products.

U.S. Pat. No. 5,841,038 discloses a remote sampling device for possibly hazardous content of a container. A hollow needle punctures the container and is used to withdraw the contents or to introduce another substance. An inert gas can be introduced into the area where the needle punctures the container.

U.S. Pat. No. 5,859,362 discloses a trace vapor detection method and device of sampling a volume of air suspected of containing drug vapors, removing particulate matter and binding vapors of the drug for further analysis. The device has a sampling, filtration and vacuum port components.

U.S. Pat. No. 6,159,422 discloses methods and apparatus for the treatment of hazardous biological waste materials. A biological waste material is placed into a chamber and a vacuum applied. Water vapor is introduced into the chamber and electromagnetic radiation energy is applied to produce a plasma.

U.S. Pat. No. 6,183,950 discloses a method and apparatus for detecting viruses using primary and secondary biomarkers. There is a sampling section for sampling the atmosphere and includes an intake device for taking a sample. It includes a heater for distilling any cholesterol and/or fatty acids from the sample. There is an analysis section for determining whether cholesterol and/or fatty acids that are indicative of the likely presence of a virus in the sample are present.

U.S. Pat. No. 6,295,860 for explosive detection system and sample collecting device in which luggage enters the device and leaves the device after inspection in which a vapor leaking from the luggage is sampled by a sampling probe, negative corona discharge is used to ionize the vapor, and a mass spectrometer is used to detect the ionized vapor to determine whether or not an explosive is present.

Patent Abstracts of Japan Pub. No. 02159554 A published Dec. 12, 1988, Application No. 63313358 discloses a monitoring method of a pathogen or allergen in which a biosensor is provided near a suction port for air conditioning provided for each room of wall surface which tends to gather mold.

WO 91/09307 published Jun. 27, 1991, for Explosive Detection Screening System detects vapor or particulate emissions from explosives and other controlled substances and reports their presence and may also report the concentration. There is a sampling chamber for collection of vapors or other controlled substances and a concentration and analyzing system, and a control and data processing system for the control of the overall system. There are a number of U.S. Pat. Nos. in this series, including the following: U.S. Pat. Nos. 4,987,767; 5,109,691; 5,345,809; 5,465,607; and 5,585,575.

SUMMARY OF THE INVENTION

Because of the huge volume of mail sent daily, a piece-by-piece inspection of the mail is not economically feasible; however, a system that detects the presence of a biohazard-containing mail piece within a few seconds of its passing through a process point would greatly simplify the identification of a biohazard-containing mail piece as well as that sub-set of mail pieces that may have likewise have been contaminated.

In view of the above, the present invention provides a system and method for detecting biohazard particulates in mail handling systems that detects the presence of a biohazard material shortly after the mail piece has been processed through machinery that functions to squeeze or compress the mail piece to expel at least some of the air in the interior volume of the mail piece and at least some of the materials therein.

Thus individual mail pieces are subjected to a squeezing or compressing action to expel some of the interior air from the mail piece and any contaminants therein at a location which is preferably as close as reasonably possible to the beginning of the mail handling and sorting line. In one preferred form, the mail handling system includes drive rollers, pinch rollers, or belt conveyors that serve to compress each individual mail piece to force at least some of the air in the interior volume of the mail piece and any material or particulates contained therein from the mail piece.

A forced air flow hood or plenum is located adjacent the mail handling system to aspirate some of the air and any air entrained materials or particles from the mail pieces as they are processed through the drive rollers, pinch rollers, or belt conveyors. The aspirated air is provided to a biohazard detection device such as a sensor suite.

The present invention advantageously provides a system and method of detecting biohazard particulates in mail handling systems.

Other features and advantages will be apparent from the following detailed description of preferred embodiments taken in conjunction with the accompanying drawings.

DESCRIPTION OF THE PREFERRED EMBODIMENTS

Figure 1:
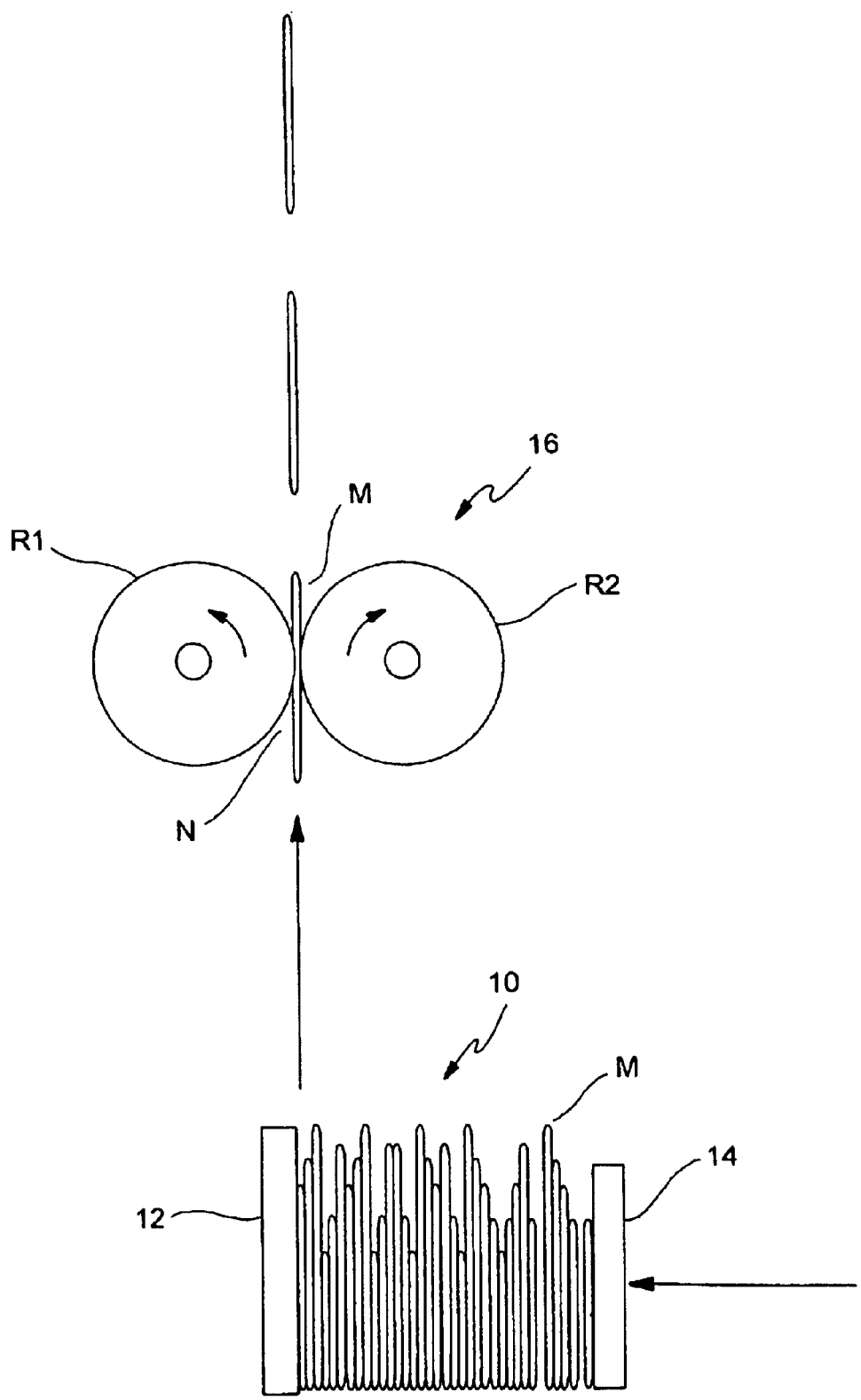
FIG. 1 is a schematic top view of a group of mail pieces in a loading hopper for introduction to a transport mechanism.

As a step in the processing of letters in U.S. Postal Service processing and distribution centers, letters pass through machines that use rollers to apply pressure to letters. It has been noted, as the result of testing, that letters filled with either talc powder and the U.S. NIST particle standard known as "Arizona Road Dust" (a standard material having ½ of its particles in the particle size range used in weaponized biological warfare agents) release plumes of particles at the point where the rollers engage the mail through a bellows effect when they are squeezed. There are other similar "pinch points", and points where letters are dropped through the air, where particle-containing letters release plumes of particles. It was at these points where anthrax dust from the letter recently sent to a U.S. senator in the capital were found. Letters laced with anthrax powder in the weaponized size range release clouds of anthrax at these points. Letters laced with other types of weaponized biological warfare agent particles, or radioactive particles, or particles of certain low vapor pressure chemical warfare agents, including VX and certain classified Russian chemical warfare agents, which disperse particulates, do the same. The agent cloud persists for a few seconds or more, a sufficient period of time for them to be collected and provided to a suite of sensors to be tested for the appropriate threats.

If, as is the case today, anthrax or other biological warfare agents are suspect agents, biological warfare agent sensors may be included in the sensor suite. If radiological particles are considered a threat, a radiological particle detector like a Geiger counter, may be included as well. For particulate chemical warfare agent threats like VX and the like, chemical warfare agent sensors like those based upon ion mobility spectrometers (IMS) or surface acoustic wave (SAW) sensors (preferably both together) may be used. The chemical warfare agent sensors often also detect particles from explosives or illicit drugs in the letters, and from residues of these materials in letters that had been contaminated by terrorists working with these materials. The purpose of the invention is to provide an enclosures about these pinch points which is vented through pumps to remove the agent from the area in the immediate vicinity of these points so that postal workers would not breath it, and simultaneously to detect the cloud of the hazardous agents and provide an alert signal so that workers could leave the area immediately and thus be safeguarded.

In one form of the invention, a shroud is placed about the point where the rollers in the USPS sorter squeeze the letters and liberate the particles by a bellow effect, or a shroud is placed around the points where letters fall through the air and are piled up at some point and release clouds of particles by the same bellows effect, a pump that pumps air from the room into the shroud, and thence outside the building through a filter, and a sensor suite, located ahead of the pump, that senses the particles in that air before the air passes through the pump and the filter and passes outside the building. The sensor suite may include sensors for whatever classes of materials are considered likely threats.

Biological warfare agents including anthrax are such a threat, and thus the BAWS I or similar sensors like the MetOne and other particle counters; BAWS III or other similar bio/non-bio detecting particle sensors like UVFLAPS and BARTS; and JBPDS and other similar complete bio detector/bio identifier sensors like Portal Shield, JBRES, 4WARN, may be used in this sensor suite. So could other developmental, advanced technology sensors.

For chemical warfare agent sensors, one may add to the sensor suite, an IMS sensor like the Environics M90 or the Environics ChemPro 100, or Graseby GID-3, or any of a range of IMX-based chemical warfare agent/explosive/illicit drug sensors made by ETG and Barringer, any of which would work. Also, SAW-based sensors including those made by LM-NE&SS-Manassas with Sandia National Laboratories, or Sandia National Laboratories alone, or Microsensor Systems of Bowling Green, Ky., or others, would work well. Because IMS and SAW sensors both exhibit false alarms, but tend to false alarm different types of materials, a combination of an IMS and a SAW sensor would be particularly useful for this sensor suite. The IMS and SAW sensors would need to incorporate heated sample inlet lines, and heated sample collection and processing front ends because the materials that they will be sampling, chemical warfare agents, explosive particles, and illicit drugs, all tend to be very sticky, and so if non-heated tubes are used to transfer samples from the air stream into the sensors, most of the particles will be stuck in the tubes and will not reach the active portion of the sensors. This known in the art. One way to do this is to heat a tape along the tubes and around the valves.

If radioactive particles are considered a threat, any one of a large number of commercial radiological sensors may be incorporated into the sensor suite. This invention is intended to apply generally to letters or packages that could release particles through physical pressure via a bellows effect or the mechanical compression that occurs when letters and packages pile up after dropping a distance through the air, and also to letters and packages that have particles on their exteriors which would be dislodged by the air that flows up from the room, over the letters and packages, into the shroud, and thence in the sampled air stream. The flow of air or the jostling of the items, would often be sufficient to dislodge particles adhering to the outsides of letters or packages.

Figure 4:
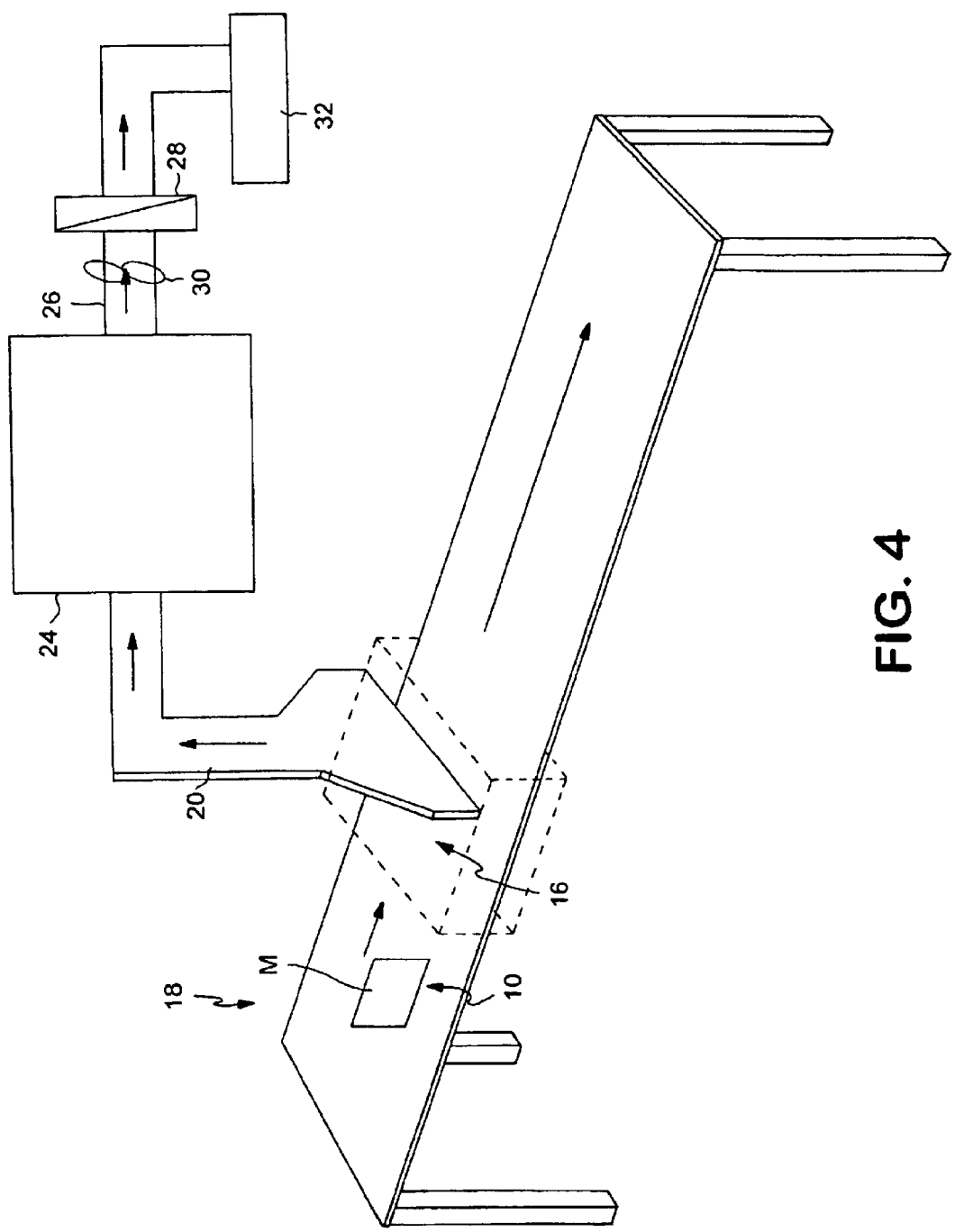
FIG. 4 is a schematic view of the entire system shown in FIGS. 1–3.

A system and method for detecting biohazard particulates in mail handling systems in accordance with the present invention is used in conjunction with conventional mail processing equipment as shown schematically in FIG. 4. As shown in FIG. 1, a stack 10 of mail pieces M, typically envelope mail in various sized standard and non-standard envelopes, is formed from envelopes positioned in a side-by-side relationship on a loading plate (not shown). One end of the stack 10 abuts a face plate 12 while a force biasing mechanism 14 at the other end of the stack 10 places a resilient biasing force on the mail pieces M to resiliently urge stack 10 against the face plate 12.

While not specifically shown in FIG. 1, a "picker" mechanism is associated with the face plate 12 to cause the mail pieces M to move in a piece-by-piece basis in the direction of the arrow into the transport mechanism 16. In FIG. 1, the transport mechanism 16 is shown as a pair of counter-rotating pinch rollers R1 and R2 defining a nip N therebetween. As the picker causes a mail piece M to enter the transport mechanism 16, the mail piece M is engaged by the two pinch rollers R1 and R2 defining a nip N therebetween. As the picker causes a mail piece M to enter the transport mechanism 16, the mail piece M is engaged by the two pinch rollers R1 and R2 to transport the mail piece M therethrough.

As the mail piece M progresses through the pinch rollers R1 and R2, the mail piece M is squeezed or compressed therebetween; since the mail piece M is typically a shape sustaining envelope having an interior air volume, the squeezing of the envelope causes a bellows type action to compress and expel some of the interior air out of the envelope into the surrounding environment. Any particulate material, including anthrax spores, will be entrained in that expelled air and be energetically introduced into the environment. In those cases where the agent particles are in the sub-micron range, they may also pass through the pores in the paper used to make certain envelopes. In either case, a mail piece M carrying a biohazard in particulate form, such as anthrax, will aerosolize some of the particulates and also contaminate the adjacent surfaces.

Figure 2:
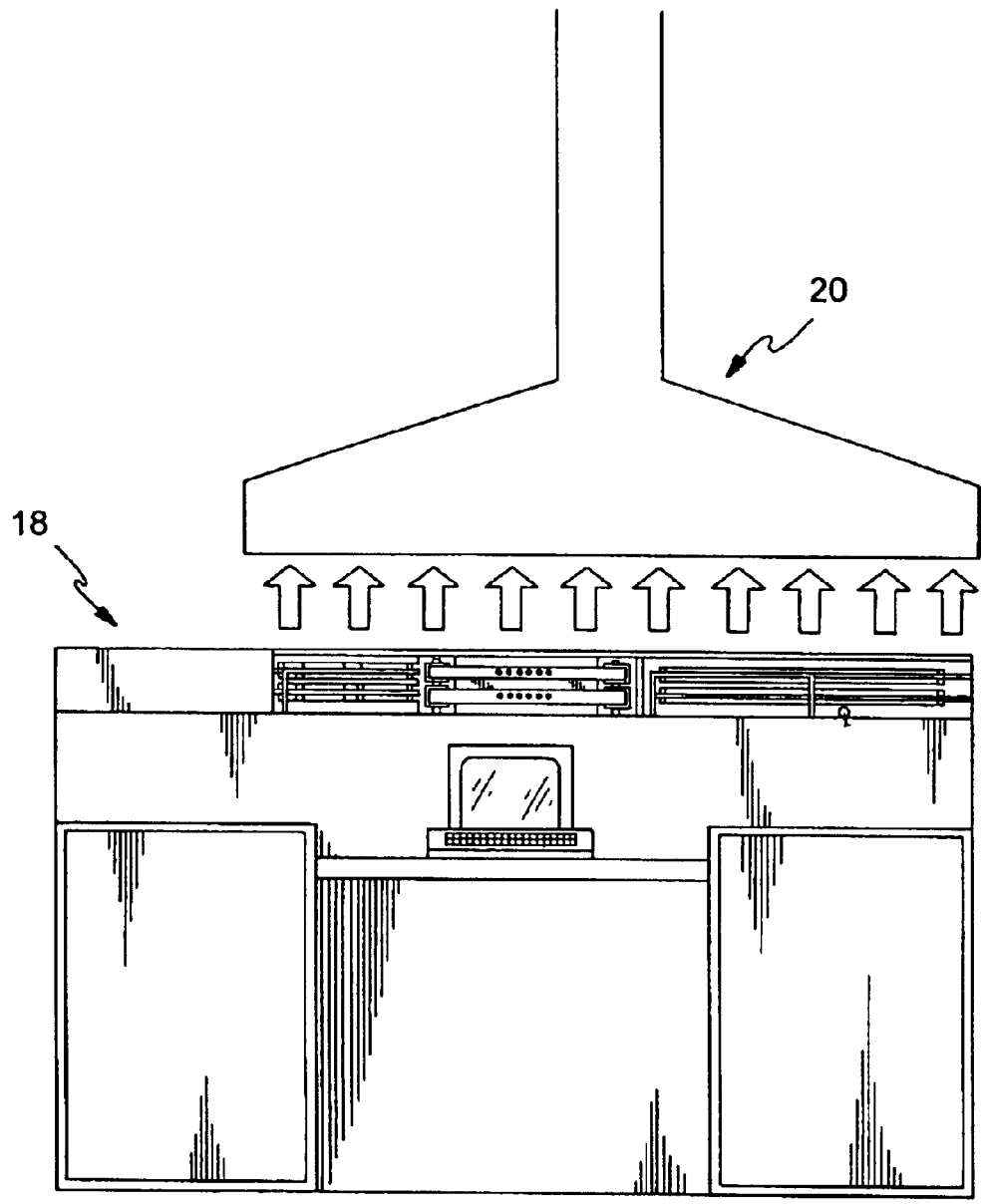
FIG. 2 is a front elevational view of a known mail processing station showing the air intake hood of the present invention above the station.

FIG. 2 is a front elevational view of a typical mail processing station 18 and is shown as an example of many known and commercially available mail processing stations of the type that use both pinch rollers and moving belts to transport the mail pieces M. However, as shown, the present invention provides an air intake hood or analytical plenum 20 which has been added to a typical station and is positioned above the mail processing station 18 and, as explained below, is designed to aspirate ambient air in the general vicinity of the mail processing station 18 and, more particularly, aspirate air immediately above those parts of the mail processing station 18 that physically transport, move, or manipulate the mail pieces M.

Figure 3:
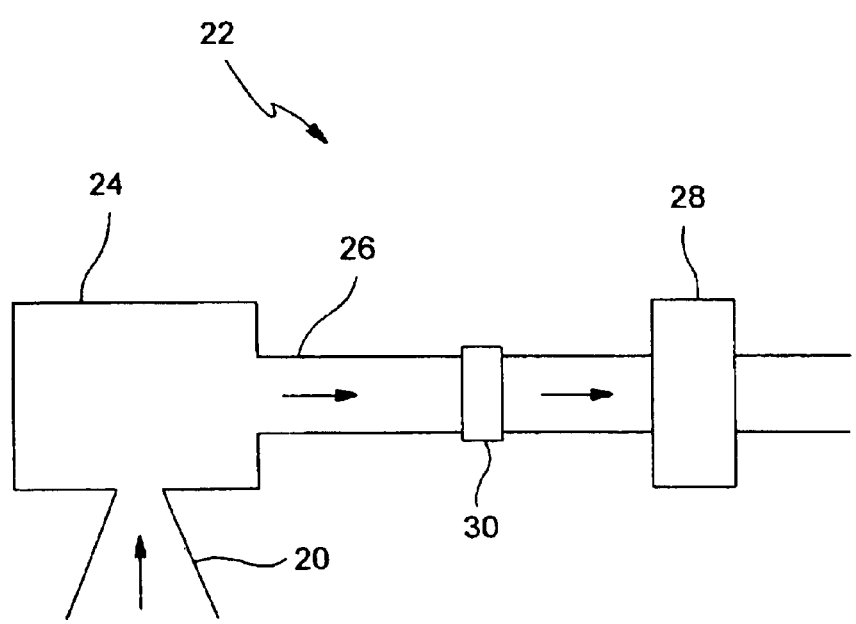
FIG. 3 is a schematic view of the air flow path for the system of FIG. 2.

FIG. 3 illustrates, in schematic fashion, the air flow handling system 22 of the present invention. FIG. 4 shows further parts of the system. The air intake hood 20 of FIG. 2 connects directly to a biohazard sensing suite 24 which, in turn, connects through an outlet duct 26 to a filter, adsorber, or scrubber 28 (or the filter can be an additional element 32 as shown in FIG. 4) that removes any biohazard material prior to exhausting the air. An air mover 30, for example, an axial or radial flow fan, is located in the outlet duct 26 and has sufficient air moving capability to draw the air in the inlet of the air intake hood into the biohazard sensing suite 24. The biohazard sensing suite 24 (typically including a plurality of diverse sensors) is connected to the air inlet hood 20 and is designed to accept the air drawn into the air intake hood 20 for analysis. The sensors can take the form as discussed above and as will be discussed below, and may be designed to detect a plurality of biological pathogens. The sensor suite is suitable to detect air entrainable particles, including bacteria, bacterial spores, viruses, rickettsia, toxins, low-volatility chemical particles including chemical warfare agent particles like VX, explosives particles, particles of illicit drugs, radioactive particles, and others, as well as vapors including chemical warfare agents, explosives and explosives related compounds, illicit drugs, hazardous industrial chemicals, and others.

The sensors could include detectors that serve only to detect the presence of biological material in particles in the analyzed air stream, like the BIONI, manufactured by Pacific Scientific Instruments of Grant's Pass, Oreg.; the Biological Aerosol Warning System Tier III developed by MIT Lincoln Laboratories in Mass.; the UV-APS, manufactured by TSI Inc. of St. Paul, Minn.; the UV-FLAPS and BARTS manufactured by General Dynamics Canada of Calgary, AB, Canada, or others. The sensors could also include a particle detector-based system like the Biological Aerosol Warning System Tier I, manufactured by Lockheed Martin of Manassas, Va. These types of sensors are preferred for the purposes of the present invention.

However, sensors could also take the form of fully-integrated, detecting and identifying biological agent sensors, utilizing UV fluorescence, as above, for detection of particles that contain biological molecules and automated immunoassay methods. There could include the Joint Biological Point Detection System (JBPDS) manufactured by Intellitec of Jacksonville, Fla., the 4WARN manufactured by General Dynamics Canada of Calgary, AB, Canada; IV fluorescence-modified Portal Shield or JBREWS manufactured by Sentel of Alexandria, Va.; or others, designed to detect and identify a plurality of biological pathogens. These type of sensors could be used because they have similar functionality, but are more expensive and larger because they perform additional functions.

Sensors for radiological particles or particles of low vapor pressure chemical warfare agents like VX could also be included in the sensor suite.

Figure 5:
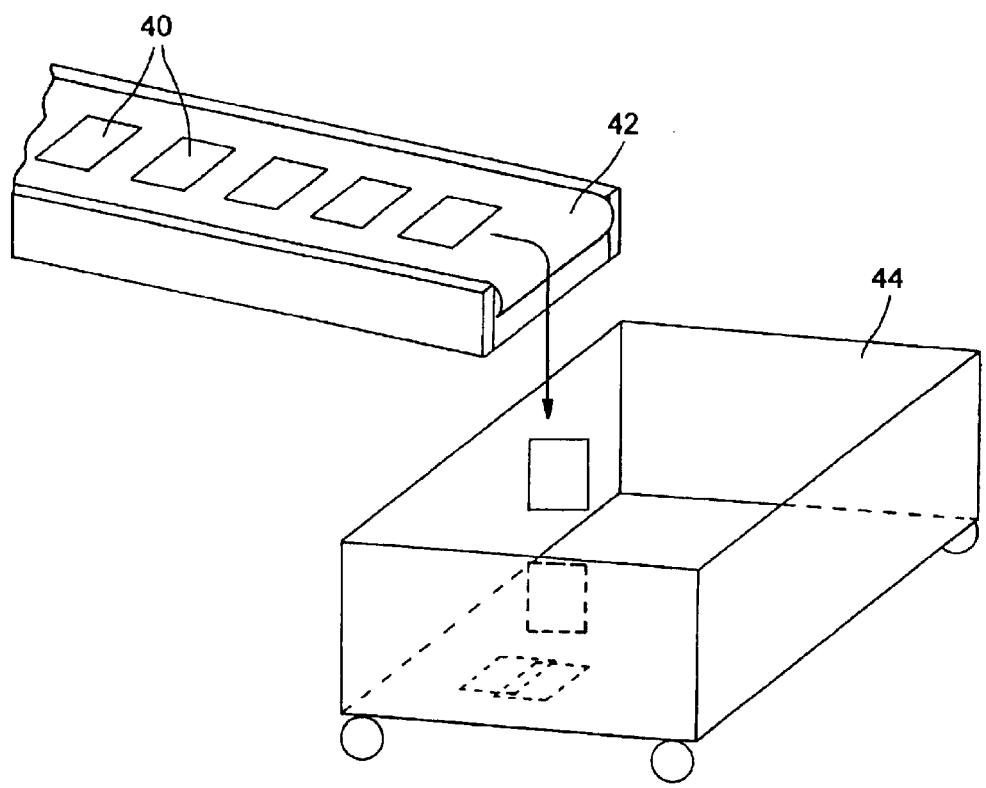
FIG. 5 is a schematic view of a portion of a mail sorting and handling line in which the mail drops from a conveyor to a wheeled bin below.

This invention may be used with letters or packages which release particles through the mechanical compression that occurs when letters and packages pile up after dropping a distance through the air. The jostling of the items will often be sufficient to dislodge particles adhering to the outsides of letters or packages. FIG. 5 shows an arrangement where the mail 40 is moved by a conveyor 42 and drops off the end of the conveyor and piles up after dropping a distance through the air. The mail drops to the bin 44 below which can be on wheels, as shown, or can be a stationary bin, or into a chute or onto a plate or table.

The present invention advantageously provides a system and method for detecting biohazard particulates in mail handling systems that function in conjunction with existing mail processing equipment to provide reasonably time efficient detection of biohazard materials in mail.

The present invention may be used with an alert system for alerting workers and a computer system that a hazard has been detected. This could be in the form of an alarm bell which rings a special code when a hazardous material is detected. It could also send an alert electronically to an enunciator, control room or remote mail control facility.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A system for detecting biohazard materials in mail comprising:
    a mail piece processing device having a transport mechanism that operates upon a mail piece to cause air in the interior volume thereof to be expelled; and
    an air transport system to transport at least some of the air expelled from the mail pieces as they are processed through the mail piece processing device into a sensor for sensing an undesired biohazard material.

2. A system as defined in claim 1 wherein the mail piece processing device provides mechanical compression to the mail pieces.

3. A system as defined in claim 1 wherein the mail processing device is one which drops the mail pieces to a lower level where the mail forms a pile.

4. A system as defined in claim 1 wherein the mail piece processing device provides pressure on mail piece to provide a bellows effect so they expel air therefrom.

5. A system as defined in claim 4 wherein the mail piece processing device is a pair of pinch rolls.

6. A system as defined in claim 4 wherein the mail piece processing device is a pair of belts.

7. A system for detecting biohazard materials comprising:
    a mail piece processing device having a transport mechanism that operates upon a mail piece to cause air in the interior volume thereof to be expelled;
    a sensor suite for sensing at least one type of undesired biohazard material; and
    an air transport system to transport at least some of the air expelled from the mail pieces as they are processed through the mail piece processing device into said sensor, including a hood which is in the vicinity of the mail piece processing device and positioned to receive all the air expelled from the mail pieces;
    said air transport system including an air duct which receives the air leaving the sensor suite and forwards same to a filter, adsorber or scrubber for removing any biohazard material therefrom and then exhausts the air into the ambient atmosphere.

8. A system as defined in claim 7 wherein the biohazard materials are air entrainable particles, including bacteria, bacterial spores, viruses, rickettsia, toxins, low-volatility chemical particles including chemical warfare agent particles like VX, explosives particles, particles of illicit drugs, radioactive particles, and others, as well as vapors including chemical warfare agents, explosives and explosives related compounds, illicit drugs, hazardous industrial chemicals, and others.

9. A system as defined in claim 7, further including a visual and/or audible alert system for alerting workers in the vicinity of the mail piece processing device that a biohazardous material has been sensed.

10. A method for detecting biohazard materials, comprising the steps of:
    a. processing mail pieces to cause air in the interior volume thereof to be expelled; and
    b. transporting at least some of the air expelled from the mail pieces into a sensor assembly for sending an undesired biohazard material.

11. A method as defined in claim 10, wherein the expelled air is collected and directed to the sensor assembly.

12. A method as defined in claim 11, wherein step a. is performed by dropping the mail to a lower lever where the mail pieces forms a pile.

13. A method as defined in claim 10 further comprising the step of forwarding the air leaving the sensor assembly to a filter, adsorber or scrubber to remove any bio-hazardous material therefrom and then exhausting the air into the ambient atmosphere.

14. A method as defined in claim 13 wherein the biohazardous materials are air entrainable particles, including bacteria, bacterial spores, viruses, rickettsia, toxins, low-volatility chemical particles including chemical warfare agent particles like VX, explosives particles, particles of illicit drugs, radioactive particles, and others, as well as vapors including chemical warfare agents, explosives and explosives related compounds, illicit drugs, hazardous industrial chemicals, and others.

* * * * *

UNITED STATES PATENT AND TRADEMARK OFFICE
CERTIFICATE OF CORRECTION

PATENT NO. : 6,834,533 B2
DATED : December 28, 2004
INVENTOR(S) : Clifford A. Megerle It is certified that error appears in the above-identified patent and that said Letters Patent is hereby corrected as shown below:

Title page,
Item [73], Assignee, change "Bethesda, MA" to -- Bethesda, MD --.

Column 8,
Line 17, "said sensor" should read -- said sensor suite --
Line 43, "sending" should read -- sensing --

Signed and Sealed this

Nineteenth Day of April, 2005

JON W. DUDAS
*Director of the United States Patent and Trademark Office*